United States Patent [19]

Brown

[11] Patent Number: 5,607,497
[45] Date of Patent: Mar. 4, 1997

[54] PASSIVE DUST SAMPLER AND METHOD OF DUST ESTIMATION

[75] Inventor: Richard C. Brown, Sheffield, England

[73] Assignee: British Technology Group Limited, London, England

[21] Appl. No.: 373,281

[22] PCT Filed: Aug. 10, 1993

[86] PCT No.: PCT/GB93/01694

§ 371 Date: Jan. 19, 1995

§ 102(e) Date: Jan. 19, 1995

[87] PCT Pub. No.: WO94/04905

PCT Pub. Date: Mar. 3, 1994

[30] Foreign Application Priority Data

Aug. 14, 1992 [GB] United Kingdom ............... 9217347

[51] Int. Cl.⁶ ............................................. B03C 3/36
[52] U.S. Cl. .................... 95/3; 55/270; 55/DIG. 39; 95/78; 96/19; 96/64
[58] Field of Search ................. 55/270, 524, 528, 55/DIG. 39; 95/57, 3, 8, 78; 96/17, 26, 60, 63, 62, 64, 18, 19

[56] References Cited

U.S. PATENT DOCUMENTS

| | | | |
|---|---|---|---|
| 3,462,995 | 8/1969 | Weiss | 73/863.21 |
| 3,763,633 | 10/1973 | Soltis | 55/524 X |
| 3,768,233 | 10/1973 | Mateson | 55/524 X |
| 4,264,331 | 4/1981 | Klein et al. | 422/98 X |
| 4,451,736 | 5/1984 | Cameron | 250/376 |
| 4,518,402 | 5/1985 | Dargel | 96/17 |
| 4,880,448 | 11/1989 | Scherrer | 96/17 |
| 4,902,306 | 2/1990 | Burnett et al. | 96/17 X |
| 4,941,899 | 7/1990 | Liu | 55/270 |
| 4,988,876 | 1/1991 | Doughty | 250/336.1 |

FOREIGN PATENT DOCUMENTS

| 0018293 | 10/1980 | France . |
|---|---|---|
| 2732491 | 10/1978 | Germany . |

OTHER PUBLICATIONS

J. Pich. "Theory of aerosol filtration by fibrous and membrane filters" Institute of Physical chemistry, Czechoslovak Acad of Sciences, Prague, Czechoslovakia, pp. 223–285, 1966.

J. H. Vincent et al., "Measurement of the static electrification of airborne dusts in workplaces" Institute of Occupational Medicine. Report No. TM/83/15, Sep. 1983, pp. 1–112.

Pillai et al, "Applications of polymer electrets for pollution studies", *Applied Physics Letters*, vol. 52, No. 18, May 2, 1988, pp.1540–1541.

Primary Examiner—Richard L. Chiesa
Attorney, Agent, or Firm—Nixon & Vanderhye

[57] ABSTRACT

A personal dust sampler hangs from a ribbon (10) attached to the user's clothing and requires no pump or power source. Dust in the air is captured by a charged PVC sheet (2) exposed at (2a) but framed by a metal foil (25) and surmounted by a metal conductor plate (6) parallel to the charged PVC sheet (2). The plate (6) is supported by conductive gridwork (3) removably attached by a flange (3) to a metal base (21). The dust captured is determined in a method by weighing or by measuring the charge loss of the PVC sheet (2).

24 Claims, 2 Drawing Sheets

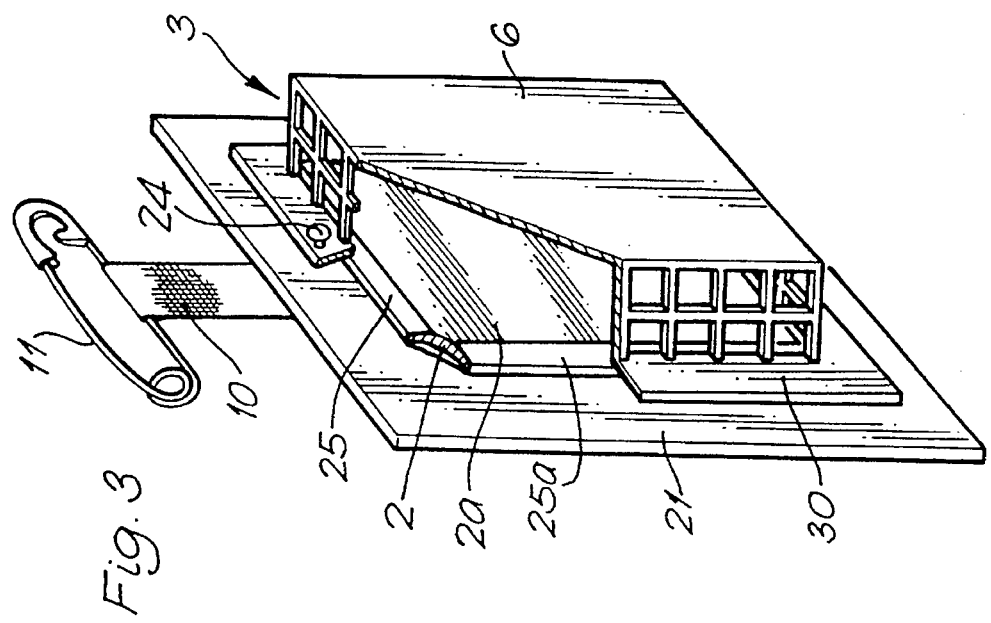
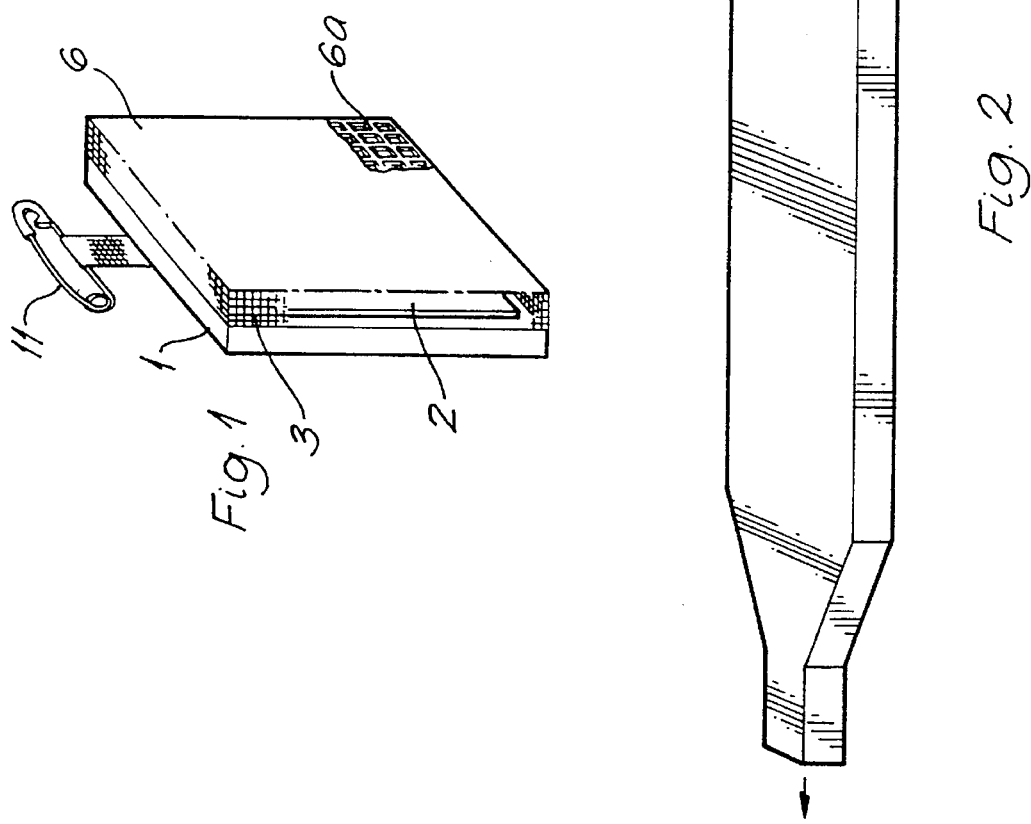

PASSIVE DUST SAMPLER AND METHOD OF DUST ESTIMATION

This invention relates to a passive dust sampler.

BACKGROUND OF THE INVENTION

Dust samplers are known in which the atmosphere containing the dust to be sampled is pumped through a collector (such as a filter medium), which traps the dust for subsequent analysis or measurement. Such a sampler requires a pump, which is bulky, and the pump in turn requires a power source, which adds to the mass and bulk. Because these samplers positively transport the dust to the collector, they may be called active dust samplers.

For personal use, it would be desirable to have a passive dust sampler, i.e. one without a pump or power source, which would sample dust at a rate proportional to its atmospheric concentration in the immediate vicinity, biassed (ideally) towards smaller particles, these generally being more harmful to the human lung. A personal sampler should also be lightweight.

A passive dust sampler must work by moving the sampled material relative to the air. Passive gas samplers make use of the diffusive motion of molecules to transport them to an adsorbing surface. Since the masses of all molecules of any chemical species are virtually identical, the average velocity of transport can be easily and accurately calculated. Dust particles also undergo diffusive motion but their average velocity is many orders of magnitude smaller than that of molecules, and so this is not an effective transport process. Capture must be brought about by external forces, and the only forces sufficiently large to be effective are gravity and electrostatic attraction.

J. Pich in Aerosol Science (1966) Ed. C. N. Davies, Academic Press, London 1966, discloses that a uniformly charged fibre captures charged particles at a rate dependent on the number of the charged particles passing per unit volume but independent of their velocity. In addition, the rate at which the charged body will collect charged particles of the opposite sign will be proportional to the electrical mobility of the particles. The electrical mobility of a particle is the velocity of the particle caused by an electric field, divided by the field strength.

If capture takes place by gravity, the same velocity-independence is observed, but the capture rate is proportional to the square of the aerodynamic diameter of the particles, and this would favour the capture of large particles and selectively exclude small ones, the opposite of what the invention seeks.

Vincent et al. in the Institute of Occupational Medicine's Report TM83/15 (1983) describe the variation of electrical mobility with particle size of industrial aerosols and find that although there is a tendency for larger particles to have a higher electrical mobility the distribution would lead to a much lower bias than that of gravitational capture.

SUMMARY OF THE INVENTION

The dust sampler according to the present invention comprises an insulator (for example an electret) in the form of a collector sheet having a known electrical charge when in use, mounted on a non-insulating base (e.g. certain glasses are sufficiently non-insulating), the sheet being surmounted by a conductor parallel thereto and preferably of at least the area of the sheet, the conductor being supported, and preferably electrically connected to the base, by (therefore preferably conductive) spacer means such as pillars or gridwork around the sheet, but preferably enclosing an area at most 110% of, or, in other cases, at least double or not more than quadruple, the sheet area. It will be understood that "non-insulator" and "conductor" are used interchangeably herein and can include not only metals etc. but also any material sufficiently conductive to be unable to retain a permanent charge, such as a semiconductor. The spacer means is for mechanical protection of the insulator and for support of the conductor, and is such that air can flow through the space between the insulator and the conductor. The spacer means may take the form of gridwork preferably not larger than 1½ cm normal to the sheet, more preferably not larger than 1 cm. Its extent in that direction is however preferably at least one-fifth of the square root of the sheet area. The gridwork may have the form of a rectangular or square-pattern mesh, in which case its extent between sheet and conductor preferably does not exceed four wefts and could be 1 weft (=pillars). Pillars could be spaced at intervals, perhaps simply at corners of the conductor.

The conductor, rectangular, nummular or otherwise, is most preferably a plate, or it may be apertured, with e.g. 0–60% of the overall area of the conductor being made up of apertures. The apertures if present are preferably at least 1 mm, but preferably not exceeding 5 mm, across, more preferably 2 to 3 mm across. The conductor, if in the form of a mesh, may be finer than the gridwork. The conductor may be physically protected by relatively stout bars (e.g. 1 $mm^2$ in cross-section and spaced apart just less than a finger's width) fixed to the base somewhat outside the gridwork.

The conductor and gridwork may be fabricated as an integral blank subsequently folded into shape, out of a mesh or by photoetching, the latter thus allowing the gridwork and the conductor to be of different patterns or pattern sizes while yet being mass-produced in one piece.

The sheet is preferably removable from the base. The conductor and gridwork are preferably removable from the base.

The sheet could be for example of polyvinyl chloride, polypropylene, polyester, PVC-acrylonitrile copolymer or polycarbonate. Other possible materials are listed in Appendix 1. Its surface electric potential should be uniform or, if not, its mean surface electric potential must be known, and could suitably be for example 1 kV. It may be either positively or negatively charged. In the case of a dust known to have an excess of particles of one sign, an electret of the opposite charge would be a good choice.

The conductor may be, or may be attached (permanently or removably) to, a carbon fibre cloth capable of adsorbing gas and hence being usable as a gas sampler, and in such a situation the conductor is preferably a plate without apertures.

The dust sampler may be for example cuboidal or nummular.

The purpose of the structure formed by the parallel conductor and supportive gridwork is to protect the collector sheet physically, to fix the electric field by which dust particle capture is effected and to reduce turbulence in any air flow past the collector sheet. The electric field is fixed in the sense that the conductor-and-grid has the same electric potential as the base, as they are in electric contact. The plane of the sheet is preferably upright during wear, to minimise the effects of gravity. Preferably the dust sampler is provided with a mounting such that it hangs upright in use.

The sampler may further comprise a second insulator in the form of a collector sheet mounted on said conductor facing the first insulator, and facing sides of the insulators may carry opposite electric charges. The invention also provides a method of dust estimation, comprising exposing a collector sheet from a sampler as set forth above, preferably while the sheet is upright, and then measuring the loss of charge from the sheet or, preferably, from a central portion only of the sheet, or otherwise determining the dust captured e.g. by weighing; other possible techniques are listed in Appendix 2). Weight gains or charge losses observed in this way tend to be small, and care must be taken to minimise gains/losses due to other causes. Where the sheet is stuck to the base, for example, an unpredictable mass of adhesive may be carried on it when it is removed for weighing. That problem can be overcome by using a metal-foil-backed insulator as the sheet; the foil, if slightly oversize, may be folded over the front of the insulator, "framing" it, and the insulator may be retained by a clip grasping the "frame" to the base or by a metal flange to the gridwork clamping the "frame" to the base. Alternatively, the collector sheet may be stuck to a rigid (e.g. glass or metal) plate, the unit (sheet+plate) taking the place of the foil and being easily removable from the base in the same way; because of its rigid format, the sheet would be easier to measure by charge scanning or microscopy, but its larger tare would make weight measurement more difficult. Where a second insulator is also present, either or both may be used to take these measurements.

Typically, a calibration factor is determined when putting this method into effect, usually from a comparison or measurements as described above with more rigorous techniques or determination of the average electrical mobility of the specific dust question. "Reference" dusts of known properties may be used to "calibrate" the samples. In certain situations, the electrical mobility may be sufficiently constant for repeated such comparisons to be dispensed with. Previous measurements by Brown et al. (Ann. Occ. Hyg. 32. 271–294 (1988)) suggest that small particles are more effective than large in reducing charge levels, and so this technique should show a bias towards small particles. Smaller particles tending to be physiologically more damaging, this bias is an advantage of the invention.

An estimating technique suitable for piezoelectric collector sheets such as PVDF is to irradiate the deposit with pulses of light of a wavelength absorbed by the deposited dust but not by other parts of the system. The energy absorbed will be converted to a quantity of heat proportional to the mass of deposited dust and this will cause the collector sheet to become heated. The consequent change in volume will cause a change in surface potential, which can be measured and related to the mass of the dust. The electret may or may not be neutralised by ionizing radiation or other means after collection and before measurement.

A further possible analysis technique might be to combine the electret substrate with a piezoelectric crystal, the natural frequency of which would be altered by the dust deposited.

BRIEF DESCRIPTION OF THE DRAWINGS

The invention will now be described by way of example with reference to and as shown in the accompanying drawings, in which FIG. 1 shows a sampler according to the invention, FIG. 2 shows electrical mobility measuring equipment which can be used in the method according to the invention, FIG. 3 shows a sampler according to the invention, being a modification of the FIG. 1 version.

DESCRIPTION OF PREFERRED EMBODIMENTS

Figure 4:
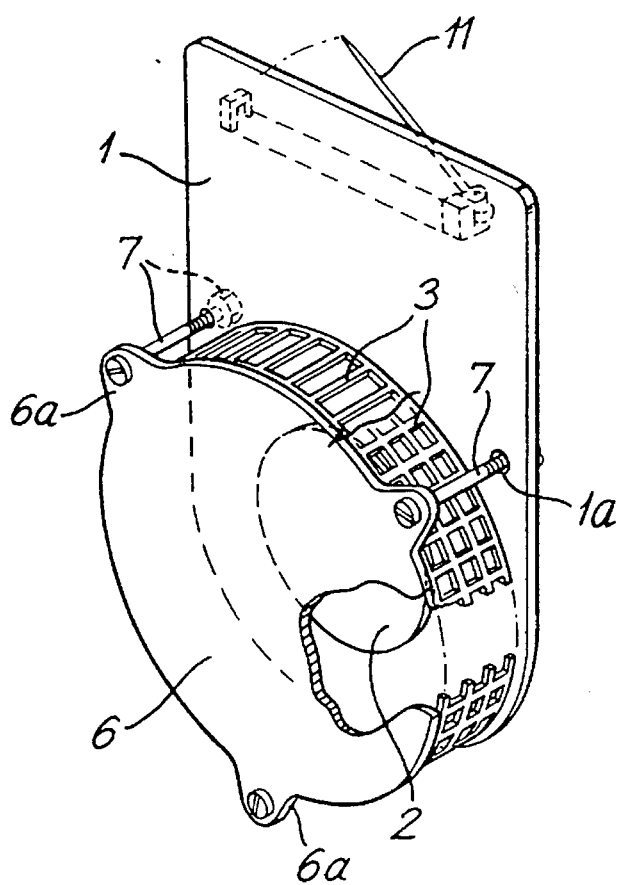
FIG. 4 shows a further sampler according to the invention.

Turning to FIG. 1, a sampler has a square base 1 of conductive glass $(3\ cm)^2$, on which is centrally mounted an insulator 2 (acting as a collector sheet) having a known electric surface potential, in this case 1.0 kV. The insulator 2 is $(29\ mm)^2$ and is of polypropylene, suitably 50 microns thick. A $(½\ cm)^2$ sheet would suffice for in-line mask sampling, but miniaturisation is not a virtue here.

Metallic gridwork 3 (part cut away for clarity) is fixed around the whole periphery of the base 1 and upstanding from it, to a "depth" of 1 cm, with wires 1 mm thick and (for averagely turbulent conditions) at 2½ mm centres. Grids finer than 2½ mm gave rise to a more uniform electric field but this was outweighed by the diminished efficiency of the sampler at collecting dust. Increasing the grid size beyond 2½ mm showed little effect. For a sampler intended for hanging on a wall in a relatively stagnant location, however, a coarser mesh could be used, e.g. 4½ mm centres, especially if the sheet does not need physical protection from poking fingers or other interference. The "depth" could be increased to say 3 cm in such an application, whereby dust depletion would be eliminated, as a problem, but a sampler to be worn on clothing would, for practical convenience, be limited to the 1 cm depth mentioned. The gridwork supports a metal sheet 6 surmounting and parallel to the electret 2 and spaced 1 cm from it. In an alternative version 6a (shown in the bottom far corner of the sheet 6), the sheet is a coarse mesh, e.g. 2 mm wires at 5 mm centres. The parts 3 and 6/6a can be integrally made as a photoetched blank which is then folded into shape. The parts 3 and 6/6a, and the electret 2 are demountable from the base 1.

The gridwork 3 and sheet/mesh 6/6a form a Faraday cage around the electret 2. A charcoal cloth (not shown) may be mounted on the outer side of the sheet 6, to adsorb gases which can then be desorbed in the laboratory and analysed. A sub-base (not shown) behind the base 1 may be larger in area and carry relatively stout bars arching in front of the sheet 6 to protect the sampler and spaced apart just less than say a finger's width.

The whole is mounted on a ribbon 10 fixed behind the base 1 and equipped with a safety pin 11 for attaching to clothing, so that the sampler, in use, is worn in the orientation shown, in particular with electret upright.

In use, the electret 2 is corona-charged, preferably uniformly, and allowed to stabilise for a week, (the stabilisation period depending on what electret material is used). It is sealed in a dust-free sachet for distribution to the user. At the place of use, it is removed from its wrapping and its charge is then assessed by a measurement of surface electric potential (e.g. 1000 V), and noted in a register. The sampler is then issued to and worn by a person exposed to dust. The conditions will normally be such that bulk drift of dust-laden air past the electret exceeds the critical velocity referred to earlier, and in the unlikely event that it is not, i.e. the air is relatively stagnant, this is easily detected by a visual or electrostatic check, which would reveal heavier dust accumulation at the edge(s) of the electret and relative depletion at the centre; such samples are noted, and will usually understate the dust concentration.

Even with the mesh 6a and if the wearer runs forwards, the increased number of dust particles passing through the Faraday cage is exactly compensated by their reduced residence time.

As to choosing between a continuous sheet 6 or a grid 6a, 6 usually leads to a more uniform dust deposit on the sheet 2, and the stagnation/depletion problem noted above is unlikely when the sampler is worn by a person undertaking normal activities.

After a predetermined period of exposure to the dusty atmosphere, the sampler is taken to (or sealed in a sachet and sent to) a non-dusty room, and the electret 2 is removed (as also the charcoal cloth if present). The loss of charge on the sheet 2 is determined by capacitative means and hence the amount of dust captured on it is estimated. A typical charge will now be 970 V, i.e. loss of 30 V. From this, the dust in the atmosphere can be assessed. Alternatively, the sheet 2 could be weighed, the weight gain since new being attributable to dust, or the deposit could be subjected to chemical analysis or, especially if the substrate is transparent, to microscopic analysis.

A fresh electret collector sheet 2 (or an old one recharged by a corona device and allowed to stabilise) is mounted on the substrate. The sampler is re-assembled and stored in a dust-proof sachet ready for issue to the next user.

The sampling rate of this device depends on the electrical mobility (and therefore the charge) on the dust particles sampled. In order for the sampler to operate correctly in all environments, the charge distribution on particles of any particular size needs to be approximately constant although, because of different mechanisms of dust formation, different atmospheric conditions, and different chemical composition and physical properties of the dust the average charge carried by particles of different dusts is likely to vary.

In order for an assessment to be quantitative the electrical mobility must be known, and so a separate assessment of this must be carried out, unless the parameter is sufficiently constant for it to be known in advance.

The measurement can be made with a device as shown in FIG. 2 consisting of a metal duct with an electret 20 (the wall furthest from the reader) having in particular a parallel conductor 26 (=wall nearest the reader) held a fixed distance above it to form a channel approximately equal in width to the electret (i.e. the electret 20 is full-height in the duct). Air from the industrial location under investigation is pumped through at a known rate, and charged particles are precipitated on to the electret forming a deposit. The extent of this deposit will depend on the electrical mobility of the particles and can be used to estimate it. The extent may be measured by means of charge scanning a reduced charge corresponding with aerosol deposit or any of the means described in relation to FIG. 1; even simply looking at the electret obliquely will be informative for an experienced operator.

If the electrical mobility of an aerosol is relatively constant at any industrial situation, this measurement could be dispensed with. In any case, even without it the passive sampler would give a good indication of relative exposure between two workers at different positions. The passive sampler may also be used in a screening mode, such that measurements made with it could be used to decide whether a rigorous conventional (expensive) dust sampling exercise should be undertaken.

FIG. 3 shows a modification of the FIG. 1 sampler, still according to the invention. Unchanged parts have the same reference numerals.

The insulator 2 is backed with a metal foil 25, which is a couple of millimetres oversize and the excess part of which is folded over the front of the insulator 2, somewhat in the manner of a picture frame.

The metal grid 3 and conductor sheet 6 span an area larger than the exposed front of the insulator 2 but smaller than the whole sheet including its "frame" 25a. The grid 3 is integral with a metal flange 30 equipped with holes for grub screws 24 for fastening the flange 30 to the base 21 (in this case of metal).

By this means, the flange 30 can clamp the insulator 2 in position without adhesive, and consistency of exposed area 2a of insulator 2 is assured by the frame 25a.

If desired, the flange 30 and/or the conductor sheet 6 may be gridwork instead of continuous sheet, the gridwork optionally being the same as 3.

As is clear from the foregoing, the device can be produced in a variety of shapes or forms. However, the analysis of collected samples will be much easier if the electret 2 is similar in shape and size to a conventional sampling filter. It should, therefore, take the form of a 25 mm diameter disc, and this consideration gives rise to the sampler according to FIG. 4, which will now be described.

The electrets 2 used in the samplers of FIGS. 1 and 3 are square, and so the grid 3/6a and base 1 natural form a cuboid, which can be formed by cutting and folding a sheet of grid material. If the electret is a disc the grid should be nummular, see FIG. 4. This shape has the advantage of having no sharp corners, but it has the drawback that it cannot easily be made from a single sheet of metal.

The field at the edge of the electret is at its weakest, especially if the grid encompasses an area not much larger than the electret, and this reveals itself by a low aerosol deposit in this region. Since uniformity of deposit will aid analysis, this observation suggests the use of a large grid. From a practical point of view however, it is important that the grid should be no larger than necessary, or it may become less convenient to wear.

The electret 2 takes the form of 25 mm diameter 23 µm-thick discs of MELINEX (Trade Mark) polyester film attached centrally to a 40 mm diameter stainless steel backing plate or base 1. No adhesive is used, electrostatic attraction being sufficient to hold the electret in place.

A cylindrical grid 3 of diameter 40 mm and height 10 mm consists of stainless steel rectangular mesh with 2⅔ mm-square holes separated by ½ mm-wide metal. Where the loss in strength can be accepted in the interests of better air flow, the intermediate circumferential metal can be omitted, as shown in part, so that the grid then consists merely of two ½ mm-wide circular strips spaced by 9 mm-high axial pillars at 3⅙ mm intervals circumferentially. The grid 3 is, in either version, capped at one end by a stainless steel disc 6 of diameter 40 mm with drilled lugs 6a, corresponding to through-holes 1a in the base 1, for interconnecting the disc 6 and base 1 by suitably long axial tamper-proof nuts and bolts 7. Air can flow easily through the 10 mm-deep space between the electret 2 and the disc 6. A pin or clip 11 attaches the sampler to clothing.

Small holes (not shown) may be provided in the base 1 to allow the electret to be poked out.

The through-holes 1a have a further function; they act as locating holes, allowing the electret to be scanned before and after dust loading, with confidence that it has remained in exactly the same position, which is useful if mechanical automated charge-monitors are used for taking the measurements.

Figure 5:
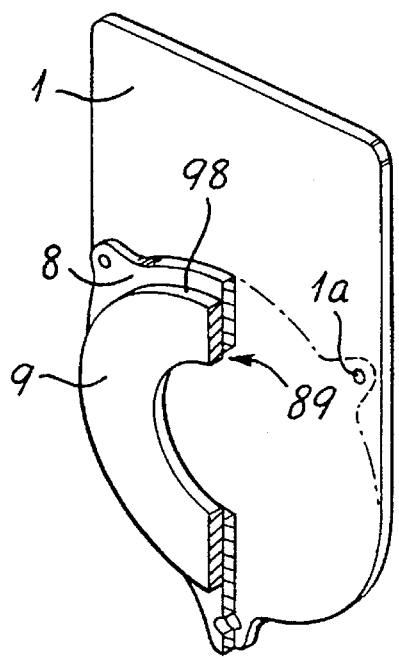
FIG. 5 shows, to a different scale and in partial section, the sampler of FIG. 4 with an electret-retaining accessory.

FIG. 5 shows in partial section (to a different scale) a modification to the FIG. 4 sampler. This modification permits the electret 2 to be stuck to a metal disc or to a glass disc such as a 25 mm diameter microscope cover slip, for subsequent X-ray or optical examination respectively. The metal or glass disc is located by a metal annulus 8 of similar thickness and 25½ mm inside diameter fitting onto the base 1, and the disc is retained by a slightly smaller overlapping annulus 9 cemented centrally on the first annulus 8. The first annulus 8 has an external diameter exceeding the 40 mm of the grid 3 and has lugs located by the nuts and bolts 7, whereby the annuli 8 and 9 are retained against sliding out of position by the action of the bolts 7 and are retained against coming off the base 1 by the presence of the edge of the grid 3, whereby in turn the electret 2 is retained in place by an inner ledge 89 formed between the annuli. The annuli form an outer step 98 which assists in locating the grid 3 when assembling the sampler.

Alternative samplers in which the grid 3 and disc 6 had diameters of 26 mm and of 33 mm were made and are useful, but the 40 mm model here described showed consistently in use the most uniform deposit of particles over the greatest area of the electret 2.

In a modification, where the conductor 6 is a continuous sheet, it too may bear an insulator e.g. electret, facing the electret 2. The sides of the two electrets facing each other are preferably of opposite charge. This arrangement assists capture of dust samples regardless of the sign of any charge which the particles may carry, and either or both of the electrets may be used in the subsequent measurements.

Appendix 1

Polymers suitable for electret production include the following:

| | |
|---|---|
| Polycyclohexyl methacrylate | (PCHMA) |
| Polyethyl methacrylate | (PEMA) |
| Polymethyl methacrylate | (PMMA) |
| Polyphenyl methacrylate | (PPhMA) |
| Polyethylene | (PE) |
| Polypropylene | (PP) |
| Polyvinyl chloride | (PVC) |
| PVC-acrylonitrile copolymer | (PVC-A) |
| Polyvinylidene chloride | (PVDC) |
| Polyvinyl fluoride | (PVF) |
| Polyvinylidene fluoride | (PVDF) |
| Polybisphenol A carbonate | (PC-n) |
| Polyethylene terephthalate | (PET) |
| Polytetrafluoroethylene | (PTFE) |
| Polyfluoroethylene propylene | (FEP) |
| Tetrafluoroethylene-hexafluoropropylene copolymer | (Teflon-FEP) |
| Tetrafluoroethylene-hexafluoromethoxyethylene copolymer | (Teflon-PFA) |
| Polyester | (MELINEX) |
| Polycarbonate | |
| Cellulose ester | |

Appendix 2

Analysis techniques suitable for determining dust include the following:
1. Gravimetric
   a) direct weighing
   b) solvent extraction, evaporation, weighing residue.
2. Chemical Analysis—In situ
   a) X-ray spectrometry (including total reflectance X-ray spectrometry and X-ray fluorescence spectroscopy such as proton-induced X-ray emission spectroscopy)—elements with atomic number ≦8 or 10
   b) X-ray powder diffraction—measures compounds rather than elements, detection limit poor—10 μg
   c) Reflected light microscopy oblique incidence X-ray or light scattering, and for translucent sheets: light extinction coefficient or transmission optical or infrared microscopy and spectroscopy
   d) Scanning electron microscopy (with energy) dispersive X-ray spectrometry and selected area diffraction)—size, shape, composition of particles.
   e) Auger spectrometry
   f) Reflectance infra-red spectroscopy
   g) UV spectroscopy
   h) Colorimetry—if the sheet has some chemical reagent that will react with the dust to provide measurable colour change
3. Dissolution of the sheet followed by Chemical Analysis—the full armoury of analytical chemistry can then be employed. For example:

| | | |
|---|---|---|
| a) | gas chromatography | |
| b) | high performance liquid chromatography | |
| c) | thin layer chromatography | } organics |
| d) | atomic spectroscopy | |
| e) | inductively coupled plasma spectrometry | |
| f) | ion chromatography - inorganic ions (sulphates, chlorides, etc.) | |
| g) | Nuclear magnetic resonance | |
| h) | micro-biological techniques | |
| i) | any of the in-situ techniques mentioned at 2 above. | | in addition, electron microscopy could be used as well as optical microscopy, and automatic counting techniques could be implemented as well.

As discussed above, it is possible to attach the electret to the body of the sampler by its electrostatic attraction. In this form the sampler is at its simplest, and there will be no adhesive to interfere with the analysis. However, certain types of analysis may require the electret to be attached to a rigid substrate. Some of the foregoing analysis techniques are discussed below, with reference to the chemical nature of the electret required and in particular to the physical form in which it is needed.

X-ray Fluorescence Spectroscopy

This technique is suitable for analysis of elements with atomic number above 8 and is used in the Occupational Medicine & Hygiene Laboratory of the GB Health & Safety Executive mainly for toxic metal analysis. During the analysis the electret, without backing, is mounted between two molybdenum masks specially designed for holding 25 mm diameter membrane filters. Polyester is a commonly used material in such analyses, and it is also suitable as an electret.

It is important that the captured material does not become detached from the substrate when it is neutralized by exposure to X-rays. Particle detachment is not, however, thought to be likely to occur because although it is the electric forces that attract particles and bring them into contact with the electret, it is principally van der Waals forces that will keep them there. These forces are not affected by neutralization of the electret material.

X-ray Diffraction

This technique is used for the analysis of both crystalline and amorphous silica. It requires the sampling substrate to be placed on an aluminium disc, which is then exposed to X-rays. The electret can be detached from the sampling base and then placed on the aluminium disc, but it would have to be neutralized before detachment. Alternatively the electret could be stuck to a thin disc of metal, which could be used in the sampler and then transferred to the X-ray equipment for analysis.

PVC-acrylonitrile copolymer is known to be a suitable material for this analysis. Polyester may be tried.

Optical Microscopy

Optical microscopy is used for the assessment of natural and man-made fibres. The sample is usually collected on a clearable membrane, which may be polycarbonate or cellulose ester. An electret with a grid ruled on it, like certain types of membrane filters, would be useful in helping the microscopist to locate the plane of the sample, especially if the deposit is sparse. It is possible that the MELINEX membrane could be used directly instead. Alternatively an electret might be stuck to a microscope cover slip (25 mm diameter 0.2 mm thick cover slips are readily available) which could then be stuck upside down on a microscope slide. The refractive index of the polymer may be important in analyses of this sort. The optical characteristics of the collector will be less important if reflected light microscopy is used.

Scanning Electron Microscopy

Preliminary measurements suggest that the electrets we have used are beam-stable, and so electron microscopy is a suitable analysis tool. Cellulose ester filters would be preferred since their use is well established. Polycarbonate would also be acceptable. Analysis of the MELINEX electret could be carried out in much the same way as that of a membrane filter sample, by examining the deposit after coating it with a thin layer of gold.

Weighing

Gravimetric analysis is most likely to be successful if samples are relatively large. Weighing of the sampler will be easier if the electret is stuck to a stable substrate like a stainless steel disc. Weighing a detached electret may be a problem because of the electric charge that it holds or might develop during handling, and in any case weighing is best carried out in a Faraday cage. Polypropylene is likely to be a good electret for this purpose because its moisture retention is low, probably about one quarter that of MELINEX (polyester). Errors caused by humidity could be reduced by sample equilibration and the use of controls, which are standard techniques in filter weighing.

Standard five-figure microbalances would give measurements to within about 20 µg for an electret weighed in its free state, and about 100 µg for an electret attached to a rigid substrate. However, the use of a six-figure microbalance—like that employed in the gravimetric estimates made on early prototypes, would give a limit of $\leq 10$ µg.

The surface of an electret is almost impermeable to deposit and so it should, in principle, be possible to remove the deposit by dissolving it, and to analyse the solution. A very important advantage of this technique is that it allows analysis to be carried out by Inductively Coupled Plasma Mass Spectrometry, which is an extremely sensitive technique capable of detecting nanogram quantities of deposit.

It is usually beneficial to dissolve the filter (or electret) along with the deposit because this makes it easier to effect quantitative transfer, improving the efficiency of the analysis. This means that the electret is better in an isolated form since the adhesive used to stick to a backing plate may complicate the analysis, and cause contamination. The ideal polymers are cellulose esters, because of their high solubility. PVC and PVC-acrylonitrile copolymer are also useful.

In this technique, the suitability of polyester is uncertain, and polypropylene is unsuitable.

I claim:

1. A dust sampler, comprising:
   a non-insulating base;
   an insulator in the form of a collector sheet having a known electrical charge when in use mounted on said non-insulating base;
   a conductor in the form of a continuous sheet surmounting and parallel to said non-insulating base and electrically connected thereto;
   upstanding apertured spacer means around the collector sheet for supporting said conductor, said conductor and said insulator being spaced apart by said spacer means to define a space therebetween, such that dust-laden air can flow through said space.

2. A dust sampler according to claim 1, wherein the insulator is an electret.

3. A dust sampler according to claim 1, wherein the conductor is of at least the area of the collector sheet.

4. A dust sampler according to claim 3, wherein the conductor and its spacer means enclose an area of at least double the collector sheet area.

5. A dust sampler according to claim 3, wherein the conductor and its spacer means enclose an area of at most quadruple the collector sheet area.

6. A dust sampler according to claim 1, wherein the conductor and its spacer means enclose an area of at most 110% of the collector sheet area.

7. A dust sampler according to claim 1, wherein the spacer means are pillars or gridwork.

8. A dust sampler according to claim 1, wherein the conductor is electrically connected to the base.

9. A dust sampler according to claim 1, wherein the spacer means space the conductor not more than 1½ cm from the collector sheet.

10. A dust sampler according to claim 1, wherein the conductor is a plate with 0–60% of its overall area being made up of apertures.

11. A dust sampler according to claim 10, wherein the spacer means are pillars or gridwork and wherein the conductor is in the form of a mesh which is finer than the gridwork.

12. A dust sampler according to claim 1, further comprising relatively stout bars physically externally protecting the conductor and fixed to the base outside the spacer means.

13. A dust sampler according to claim 1, wherein the conductor and spacer means are fabricated as an integral blank subsequently folded into shape.

14. A dust sampler according to claim 1, wherein the collector sheet is removable from the base.

15. A dust sampler according to claim 1, wherein the conductor and spacer means are removable from the base.

16. A dust sampler according to claim 1, wherein the collector sheet is selected from the group consisting of polyvinyl chloride, polypropylene, polyester, PVC-acrylonitrile copolymer and polycarbonate.

17. A dust sampler according to claim 1, wherein the conductor is permanently or removably attached to a carbon fiber cloth capable of adsorbing gas.

18. A dust sampler according to claim 1, further comprising a mounting arranged in use to hang the dust sampler such that the plane of the sheet is upright.

19. A dust sampler according to claim 1, further comprising a second insulator in the form of a collector sheet mounted on said conductor facing the first insulator.

20. A dust sampler according to claim 19, wherein the facing sides of the insulators carry opposite electric charges.

21. A method of dust estimation, comprising the steps of: exposing to dust a dust sampler comprising a non-insulating base, an insulator in the form of a collector sheet having a known electrical charge when in use mounted on said non-insulating base, a conductor in the form of a continuous sheet surmounting and parallel to said non-insulating base and electrically connected thereto, upstanding apertured spacer means around the collector sheet for supporting said conductor, said conductor and said insulator being spaced apart by said spacer means to define a space therebetween, such that dust-laden air can flow through said space; and determining the dust captured by the collector sheet.

22. A method according to claim 21, wherein the determination is by weighing.

23. A method according to claim 21, wherein the determination is by measuring the loss of charge from the sheets.

24. A method according to claim 23, wherein the loss of charge is measured from a central portion only of the sheets.

* * * * *